(12) United States Patent
Rippstein, Jr.

(10) Patent No.: US 6,193,695 B1
(45) Date of Patent: Feb. 27, 2001

(54) DISPOSABLE SAFETY SYRINGE HAVING A RETRACTABLE NEEDLE

(76) Inventor: Wayland J. Rippstein, Jr., Route 2, Box 820, Alvin, TX (US) 77511

( * ) Notice: Subject to any disclaimer, the term of this patent is extended or adjusted under 35 U.S.C. 154(b) by 0 days.

(21) Appl. No.: 09/483,225

(22) Filed: Jan. 14, 2000

(51) Int. Cl.[7] ................................................. A61M 5/32
(52) U.S. Cl. ......................................... 604/195; 604/110
(58) Field of Search .................................. 604/195, 192, 604/198, 187, 110, 263

(56) References Cited

U.S. PATENT DOCUMENTS

| | | | |
|---|---|---|---|
| 4,425,120 | * | 1/1984 | Sampson et al. . |
| 4,643,200 | * | 2/1987 | Jennings, Jr. . |
| 4,675,005 | * | 6/1987 | DeLuccia . |
| 4,692,156 | * | 9/1987 | Haller . |
| 4,747,830 | * | 5/1988 | Gloyer et al. . |
| 4,790,822 | * | 12/1988 | Haining . |
| 4,816,022 | * | 3/1989 | Poncy . |
| 4,908,022 | * | 3/1990 | Haber . |
| 5,000,736 | * | 3/1991 | Kaufhold, Jr. et al. . |
| 5,885,257 | * | 3/1999 | Badger . |

* cited by examiner

Primary Examiner—John D. Yasko
(74) Attorney, Agent, or Firm—Browning Bushman

(57) ABSTRACT

A disposable syringe assembly generally including a cylinder assembly 10, a needle assembly 20, a piston assembly 30, a seal cap assembly 40, a piston stem 50 and handle 60. The cylinder assembly 10 may be engaged with the needle assembly 20 substantially near the needle end of the cylinder assembly 10 and the cylinder assembly may be engaged with the seal cap assembly 40 near the seal cap end of the cylinder assembly 10. The cylinder assembly 10 may further including a fluid region 14 and an air region 15. As fluid is drawn into the fluid region 14 by movement of the piston assembly 30, air is displaced from the air region 15 through a one-way valve. As fluid is discharged from the cylinder assembly 10, a low pressure is created in the air region 15. When substantially all fluid is discharged from the cylinder assembly, a connector on the piston assembly 30 may engage a connector on the needle assembly 20, and the needle assembly 20 may be disengaged from the cylinder assembly 10 and the needle assembly 20 may be retracted into the cylinder assembly 10.

16 Claims, 3 Drawing Sheets

DISPOSABLE SAFETY SYRINGE HAVING A RETRACTABLE NEEDLE

FIELD OF THE INVENTION

The present invention relates generally to medical instruments and more particularly to a disposable syringe having a retractable needle. More specifically this invention relates to a syringe which, during injection or displacement of the contents of the syringe from the syringe, a vacuum is created within the syringe body which may, upon completion of the injection, automatically retract the needle inside of the syringe body to prevent accidental needlesticks.

BACKGROUND OF THE INVENTION

Health care workers routinely risk exposure to communicable diseases through accidental exposure to contaminated medical products, waste products and bodily fluids. One of the largest exposure risks to healthcare workers and handlers of related hazardous waste is from accidental needlesticks or scratches from used hypodermic syringes. The Centers for Disease Control and Prevention reports that there are in excess of one-half million reported accidental needlesticks each year and an estimated three million additional needlesticks not reported. It is further reported that the odds of a healthcare worker contracting human immunodeficiency virus (HIV) alone through a needlestick are one in 300. The odds of a healthcare worker contracting any of many other serious or potentially fatal diseases such as hepatitis are even greater. In response to this health issue some states are enacting legislation requiring exclusive use of safety hypodermic syringes with retractable or protected needles.

Numerous solutions to the needlestick problem have been proposed, including U.S. Pat. No. 4,790,822, which discloses a disposable syringe in which the needle can be captured by a plunger and then fully retracted into the barrel of the syringe. The plunger shaft may then be broken off flush with the end of the barrel such that the needle may not be mechanically projected to extend beyond the opposite end of the barrel.

U.S. Pat. No. 4,747,830 discloses a similar system including a plunger that can be broken off once the needle is fully retracted into the barrel of the plunger. U.S. Pat. Nos. 4,692,156 and 4,675,005 both disclose disposable syringes wherein the needle can be fully retracted into the barrel of the plunger. U.S. Pat. No. 4,643,200 discloses a similar system used with a blood donor assembly, which allows retraction of a needle into a barrel.

U.S. Pat. No. 4,425,120 discloses a movable needle guard conduit which extends from the barrel of the syringe over the full length of the needle. The needle guard may be retracted during use of the syringe and may then re-extend to cover the needle following use of the syringe. U.S. Pat. No. 4,816,022 discloses a syringe with a sliding cap which utilizes a nub and backseat for engagement of a nosepiece for securing the cap around the syringe. U.S. Pat. No. 3,008,570 discloses a removable cap for enclosing and protecting a sterilized syringe in a moveable housing.

U.S. Pat. No. 5,000,736 discloses a syringe including a tubular plunger from which air has been evacuated which upon use may retract the needle into the plunger by differential pressure. U.S. Pat. No. 5,885,257 discloses a syringe which utilizes a compressed spring placed between a needle carrier and the barrel of the syringe and including a releasable retaining means to hold the needle carrier in position until retraction is desired. U.S. Pat. No. 4,908,022 discloses a disposable safety syringe including a cylinder which is pre-filled with fluid medication, a double ended needle and a plunger. Following use of the syringe, the end of the needle which extends into the barrel may penetrate the piston such that the needle may be manually withdrawn into the barrel by axial retraction of the plunger which remains in engagement with the needle.

Thus, a variety of prior art retractable syringes are known. Prior art syringes, however, have not offered a universally acceptable solution to the needlestick issue.

Healthcare workers throughout the world may benefit from a syringe which reduces or eliminates the risk of accidental needlestick or exposure to contaminated surfaces such as the exterior surface of a used needle, by overcoming the disadvantages of prior art syringes. An improved syringe is desired which is simple in design, manufacturing and operation so as to be widely applicable, cost effective, reliable and which does not require pre-filling with medication or fabricating with stored potential energy. A syringe is also desired which may become an industry standard through overcoming the disadvantages of prior art.

The disadvantages of the prior art are overcome by the present invention and an improved retractable needle syringe is hereinafter disclosed which has particular utility in protecting healthcare and sanitation workers.

SUMMARY OF THE INVENTION

The present invention is a hypodermic syringe apparatus (syringe) that may retract a hypodermic needle into a syringe body after the syringe contents have been discharged, so as to prevent accidental needlesticks, scratches or other exposure to healthcare workers of contaminated needles or fluids thereon. In addition to protecting healthcare workers, this invention may also prevent the multiple use or sharing of syringes and needles. This invention may also protect workers involved with disposal and sanitation of used syringes and may reduce the likelihood of infectious particulates becoming airborne. The syringe may preferably be a disposable, single use type and may be available in various standard and non-standard sizes and shapes.

It is an object of the present invention to provide an improved vacuum operated, retractable-needle syringe. A preferred embodiment of this invention may include: (a) a selectively retractable needle assembly including a hypodermic needle and apparatus for supporting and engaging the hypodermic needle; (b) a cylindrical syringe body that may serve as both a reservoir for injectable or withdrawn fluids and a vacuum chamber; (c) a piston assembly that serves to draw fluids into the syringe body or discharge fluids contained within the syringe body, and to assist in producing a vacuum; (d) a seal cap assembly including a cap for engaging and sealing with the cylindrical body and a one-way valve assembly that may permit air flow only out of the syringe, thereby also assisting in producing a vacuum within the cylinder body; and (e) a piston stem and handle for manipulation of the piston assembly. It is expected that all seals referenced herein are pneumatic seals and that all pneumatic seals also form hydraulic seals.

The needle assembly of the syringe may be selectively retractable in that the plunger may be manually manipulated in either direction within the cylinder body and intermittently halted at substantially any position along the usable portion of the cylinder body, without attaching to the needle assembly for purposes of retracting the needle until the practitioner so desires to retract the needle by connecting the retracting connectors and disengaging the needle assembly from the cylinder body, as disclosed below. The hypodermic needle may be placed into a vial or subcutaneous, to draw fluids into the syringe cylinder body. Fluid may be drawn into the cylinder body of the syringe by axially moving the piston assembly from a first end of the syringe cylinder body near the needle assembly to a second end of the syringe cylinder body near the seal cap assembly. The piston assembly is moveably in pneumatic sealing engagement with the inner wall of the syringe body.

It is an object of the present invention to provide a piston and valve operated mechanism for creating and maintaining potential energy within the syringe, during use of the syringe for retracting the needle assembly upon completion of syringe use. Continuing with the description of the preferred embodiment, during filling of the syringe cylinder body with fluid, as the piston assembly is displaced from the needle end of the cylinder body to the seal cap end of the cylinder body, the air between the piston and the seal cap is displaced out of the syringe through the one-way valve assembly. As the fluid is discharged from the syringe by moving the piston toward the needle end of the cylinder body, a low pressure region is created between the piston and the seal cap, thus creating potential energy within the syringe.

During the fluid discharge movement of the piston toward the needle end of the syringe, this potential energy is effected in the syringe body by the creation of a low pressure and relatively large volume region within the cylinder body, as a force sufficient to retract the connected needle assembly into the cylinder body after the needle assembly retainer is mechanically sheared. When the fluid is substantially fully discharged, a connector attached to the piston assembly may engage with a connector on the needle assembly. If it is desired by the practitioner for the needle assembly to retract into the cylinder body after completion of the fluid discharge from the syringe, a small increase in axial force upon the piston stem may attach the piston connector to the needle connector, and thereby shear the retainer components which were engaging the needle assembly to the cylinder body. Shearing the retainer components also ruptures a pneumatic seal between the needle assembly and the cylinder body such that the needle end of the piston assembly is exposed to ambient atmospheric pressure.

Upon attachment of the connectors, the axial connecting and shearing force that is applied by the practitioner acting upon the piston stem may be relaxed. The ambient atmospheric pressure external to the needle assembly and piston assembly may act axially through the needle assembly and through the needle end of the cylinder body, and act upon the needle side of the piston assembly, in the axial direction of the seal cap. This pressure force may be referred to as a gross retracting force. The gross retracting force acts in opposition to an opposing force created by atmospheric pressure acting axially upon the piston stem, in the direction of the needle assembly. Although the ambient atmospheric pressure in both the gross retracting force and the opposing force are substantially equal, the area upon which each force acts is significantly different, such that the gross retracting force is substantially larger than the opposing force. The difference in the gross retracting force and the opposing force, represented essentially as a relatively low pressure volume within the cylinder body, may yield a net retracting force upon the piston assembly in the axial direction of the seal cap assembly which is of sufficient force as to move the piston assembly, needle assembly and piston stem, and fully retract the previously disengaged needle assembly within the cylinder body.

In a preferred embodiment, the needle assembly may be retained and supported in a stationary position in the syringe cylinder body, partially by the shearable retaining components. In a preferred embodiment, the cylinder body may include a frustoconical taper near the needle end of the cylinder body in order to stabilize or support the needle assembly which is engaged with the cylinder body. The additional connecting and disengaging force applied to the piston stem by the practitioner is sufficiently greater than the shear value of the retaining components which hold and support the needle assembly in position in the syringe cylinder body, so as to facilitate shearing the retaining components. Upon shearing, the needle assembly which, as discussed above may be connected with the piston assembly, may move axially through the syringe cylinder body as the piston is displaced by the energy effected by the low pressure region in the cylinder body, from the needle end of the syringe cylinder body toward the seal cap end of the syringe cylinder body. The result is a fully encased and protected hypodermic syringe needle.

It is a feature of the present invention that the retractable syringe is simple to operate and economical manufacture. It is also a feature of the present invention that the syringe is highly reliable and may fully perform its intended purpose, which is to facilitate a hypodermic injection and/or withdrawal and then fully retract and retain the used hypodermic needle within the syringe cylinder body, immediately upon completion of use.

Although preferred embodiments are disclosed, other embodiments may naturally evolve from the concepts of this invention and as such remain within the scope of this invention. Several alternative embodiments are disclosed in the attached drawings and detailed specifications. The concepts of this invention may be applied to syringes for use in hypodermic injections and withdrawals, including blood donation apparatus, intravenous (IV) catheter uses and related medical and technical equipment employing a potentially penetrating or scratching hypodermic needle.

BRIEF DESCRIPTION OF THE DRAWINGS

FIG. 6 is a cross-section view of an alternative embodiment illustrating a stop lever embodiment.

DETAILED DESCRIPTION OF PREFERRED EMBODIMENTS

Figure 1:
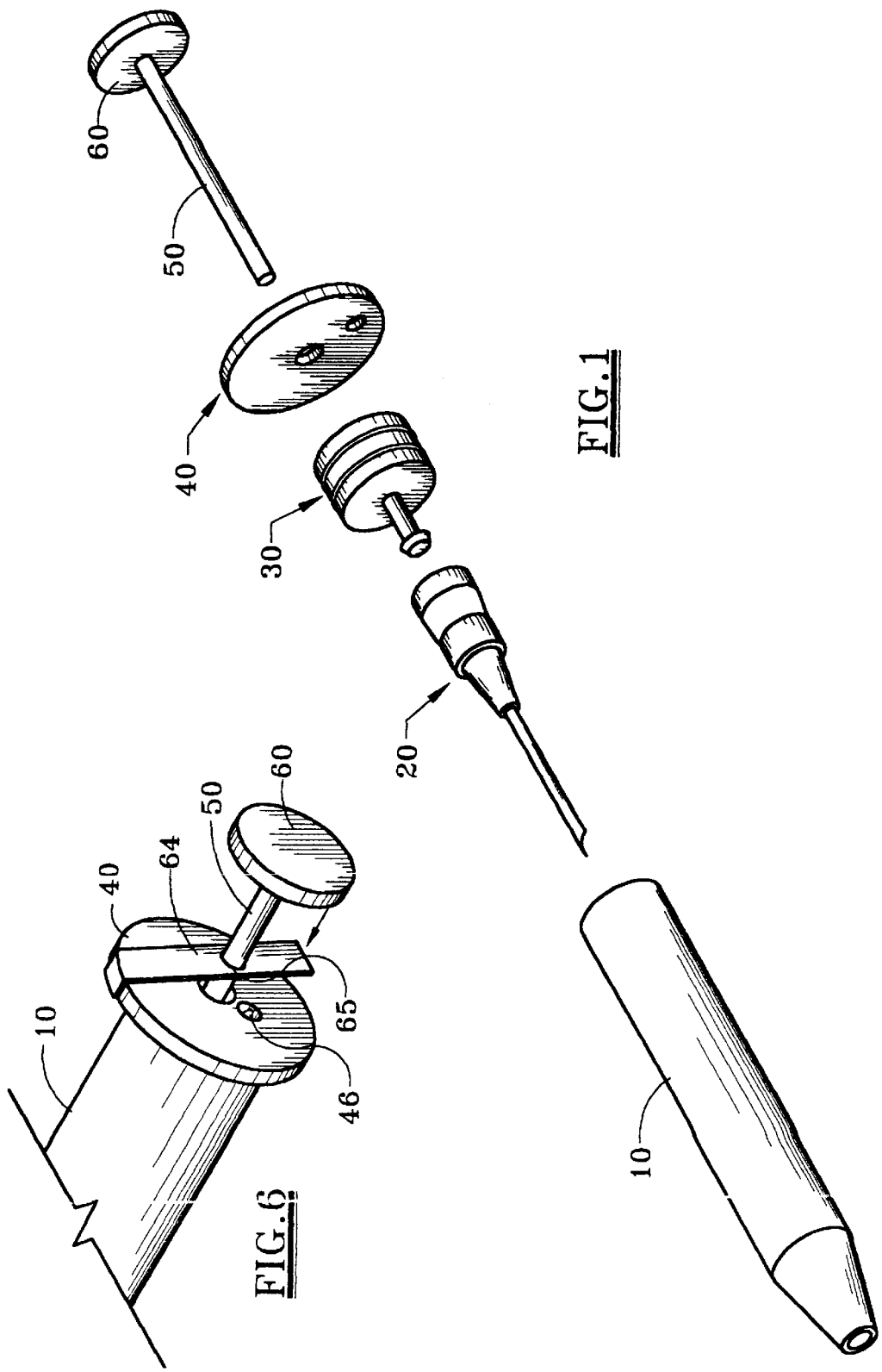
FIG. 1 is an exploded view of an embodiment, generally illustrating major components.
Figure 2:
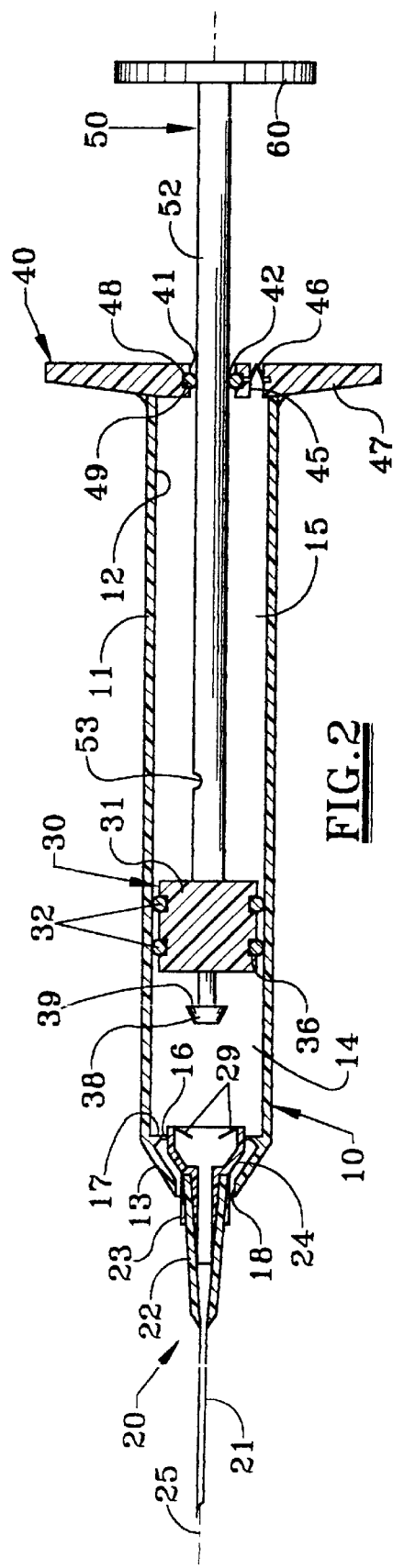
FIG. 2 is a cross-section view of a preferred embodiment of a syringe assembly, illustrating the needle attached with the cylinder assembly.
Figure 2A:
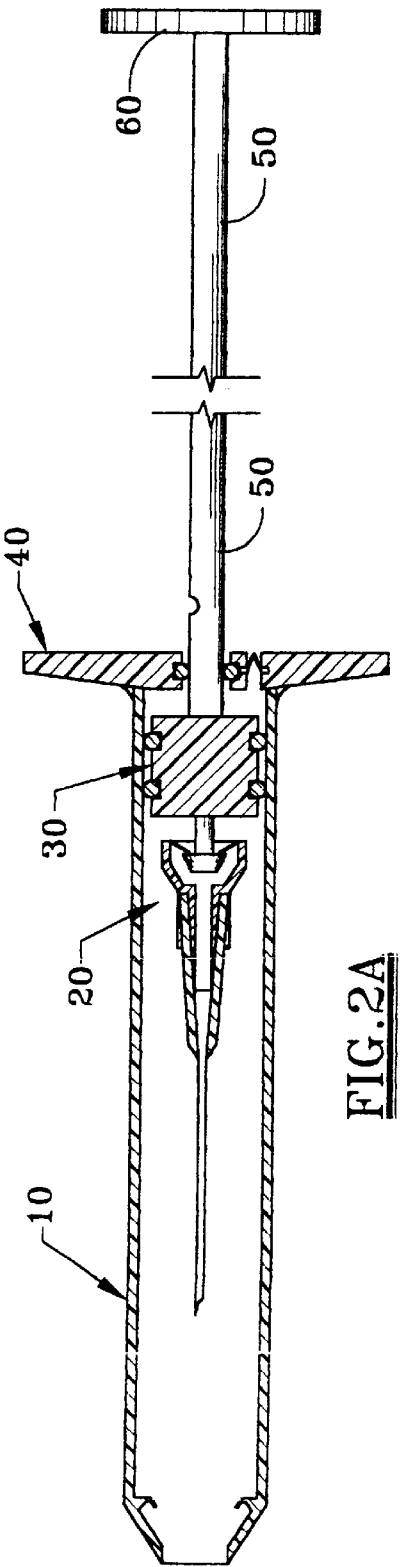
FIG. 2A is a cross-section view of the syringe assembly illustrated in FIG. 2, with the needle assembly connected to the piston assembly and the needle assembly in the retracted position.

FIGS. 1, 2 and 2A illustrate a suitable embodiment for a hypodermic syringe apparatus that may retract a hypodermic needle into a syringe body according to the present invention. Referring to FIG. 1, the syringe apparatus may generally include (a) a cylinder assembly 10; (b) a needle assembly 20; (c) a piston assembly 30; (d) a seal cap assembly 40; (e) a piston stem 50; and (f) a handle 60.

As illustrated in FIG. 2, the cylinder assembly 10 may include a cylinder body 11 having a needle end and a seal cap end, a through bore along a central axis 25 of the syringe assembly, the central axis 25 extending axially through the center of the through bore along the cylinder assembly 10. The cylinder assembly 10 may include a closure portion 13, having a portal opening 18 for penetration by a needle assembly 20, the closure portion 13 being substantially near the needle end of the cylinder assembly 10. The closure portion 13 and the side of the portal opening 18 may each assist to support and retain the needle assembly 20 in static position near the needle end of the cylinder assembly 10. In addition, the cylinder assembly 10 may include a radial retainer supporting projection 17 and a retainer 16 for assisting in retaining and supporting the needle assembly 20 near the needle end of the cylinder assembly 10. In a preferred embodiment, the retainer 16 may be a retainer ring and may be shearable so as to selectively disengage and unseal the needle assembly 20 from the cylinder assembly 10. In an alternative embodiment, the retainer 16 may not shear and the retainer supporting projection 17 and/or the retainer 16 may provide a friction fit engagement between the needle assembly 20 and the cylinder assembly 10. The retainer ring 16 and/or the friction fit engagement may provide a pneumatic seal between the needle assembly 20 and the cylinder assembly 10, thus forming a portion of a fluid chamber 14 within the syringe assembly. In this invention, all pneumatic seals are also presumed to also be hydraulic seals.

Figure 3:
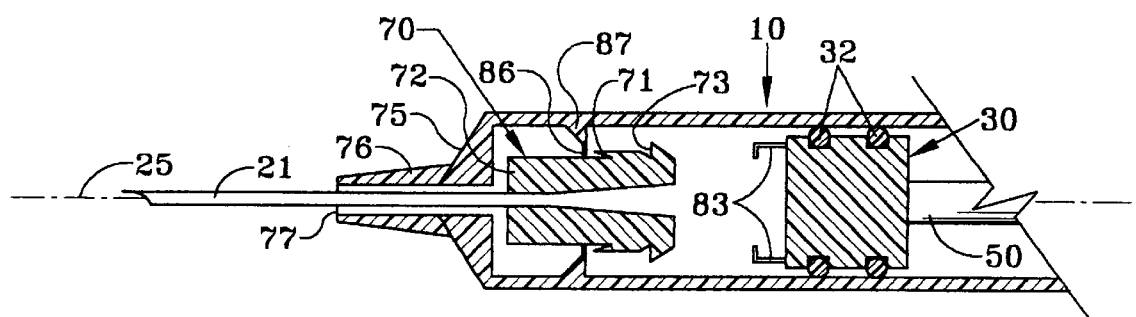
FIG. 3 is a cross-section view of some alternative embodiments.

A preferred embodiment of the syringe assembly as illustrated in FIG. 2 may also include a needle assembly 20. The needle assembly 20 may include a hypodermic needle 21, which may be affixed to the needle assembly 20 by engagement of the hypodermic needle 21 with a substantially cylindrical needle attachment component 22. The needle attachment component 22 may be engaged with a substantially cylindrical needle assembly base 24. The needle assembly base 24 may be engaged with the needle attachment component 22. A substantially cylindrical needle assembly bushing 23 may also be included, the needle assembly bushing 23 substantially radially encompassing a portion of both the needle attachment component 22 and the needle assembly base 24. The needle assembly 20 may also include a needle assembly connector 29, such as, in a preferred embodiment, an inward oriented radial flange, which may be represented as a female connector component. Alternatively, as illustrated in FIG. 3, the needle assembly 20 may include a male connector component 73.

As illustrated in FIG. 2, the syringe assembly may also include a piston assembly 30, which may include a piston 31 and one or more piston seals 32. Piston seals 32 may include one or more radial grooves 36 for housing O-rings 37. Alternative embodiments of the piston assembly 30 may include piston seals 32 which are formed as an integral part of the piston 31. Piston seals 32 may form a pneumatic seal between the piston 31 and the inner wall 12 of the cylinder body 11. The piston 31 may move axially within the cylinder body 11, along the central axis 25. The piston assembly 30 may provide on one side of the piston 31 for attachment of the piston 31 to a piston stem 50. The piston assembly 30 may provide on the other side of the piston for attachment of the piston 31 to a piston connector 38. The piston connector 38 may include, in a preferable embodiment, a male type piston connector which may include a shoulder 39 for locking the piston connector component 38 to a female needle assembly connector 29.

A preferred embodiment of the syringe assembly may also include a seal cap assembly 40. The seal cap assembly may include a seal cap 47, which may be connected to the seal cap end of the cylinder assembly 10, the connection forming a pneumatic seal between the seal cap 47 and the cylinder body 11. The seal cap 47 may include a stem port 41 for the penetration and reciprocation of a piston stem 50 through the seal cap 47. In order to seal the annular area in the stem port 41 between the stem 50 and the seal cap 47, the stem port 41, may include a stem seal 42, such as a groove 48, to house an O-ring 49. The seal cap assembly 40 may also include a valve port 45, in the seal cap 47. The valve port 45 may include a one-way valve 46 which may allow the evacuation of air from within an air region 15 in the cylinder body 11, substantially near the seal cap end of the cylinder assembly 10. The one-way valve 46 may assist in effecting a pneumatic seal between the air region 15 in the cylinder body 11 and the atmosphere external to the seal cap 47 to prevent the undesirable flow of air into the air region 15.

The syringe assembly as illustrated in FIG. 2 may include a piston stem 50, which may penetrate the piston stem port 41 in the seal cap assembly 40. The piston stem 50 may attach to the piston assembly 30 on one end and to a handle 60 or any other control or actuating component on the opposite end. The piston stem 50 may include a reduced diameter segment 53 substantially near the piston end of the piston stem 50, so as to provide a preferred point to break the piston stem subsequent to use of the syringe to prevent subsequent displacement of the piston assembly 30 and connected needle assembly 20 toward the needle end of the cylinder assembly 10, and to further disable the syringe from subsequent use.

The needle assembly 20 may be positioned within the cylinder assembly, substantially near the needle end of the cylinder assembly 10, but with a relatively small gap between the needle assembly 20 and a side piston side of the closure portion 13 of the cylinder assembly 10. This gap may be such that when the retainer 16 is sheared or the friction fit ruptured, the needle assembly 20 may axially move along the center line 25, relative to the cylinder assembly, toward the needle end of the cylinder assembly 10 to facilitate shearing of the retainer 16. Components of this invention may be manufactured from various combinations of rigid thermo-plastics, metallic materials, composites, polymers and elastomers, in varying material combinations as appropriate for the desired application and economics.

In operation of the syringe assembly of this invention, in a preferred embodiment as illustrated in FIG. 2, the syringe may be shipped with the piston 31 substantially near the needle end of the cylinder assembly 10, such that a connector 38 on the piston assembly 30 may be substantially adjacent the connector 29 on the needle assembly 20. In this position, the connectors 29, 38 are not connected to each other. By manual manipulation of the syringe assembly, the hypodermic needle 21 may be inserted into a vial, subcutaneous in a patient or placed into any other vessel from which it is desirable to draw fluid into the fluid region 14 of the syringe assembly. The practitioner may then apply an axial pulling force along the center line 25 of the syringe assembly, upon the handle 60, in the direction away from the needle end of the cylinder body 11. The handle 60 or other actuating component may be attached to the piston stem 50 and the piston stem 50 may be attached to the piston assembly 30. The term handle may include a device or component to facilitate manual or automatic manipulation of the stem and/or piston, or any other control, actuating or manipulation device or component which may facilitate manual or automatic manipulation of the piston 31. The axial force which may be applied substantially to the handle 60, may cause the piston assembly 30 to be axially displaced from substantially near the needle end of the cylinder assembly 10, toward the seal cap end of the cylinder assembly 10. As the piston is displaced toward the seal cap assembly 40, fluid may be drawn into a fluid region 14 in the cylinder body 11 between the piston 31 and the needle assembly 20. Simultaneous with the drawing of fluid into the fluid region 14 of the cylinder body 11, air, from an air region 15 in the cylinder body 11 between the piston 31 and the seal cap assembly 40, may be displaced from within the air region 15, through the one-way valve port 45 and one-way valve 46. During this movement of the piston 31 toward the seal cap end of the cylinder body 11, the piston 31 may be halted at any desired position within the cylinder body 11 so as to maintain a static position of the piston 31 relative to the cylinder body 11, having no stored mechanical energy in the mechanism of the syringe assembly. Thus, the piston may remain stationary until the practitioner desires to either draw more fluid into the syringe body 11, or displace the fluid from the syringe body.

When it is desired to displace the fluid from within the fluid region 14 of the cylinder body 11, the practitioner may apply an axial force to the handle 60 or other actuating component, along the center line 25, toward the needle end of the syringe assembly. As this force is increased, the piston assembly 30 may move toward the needle end of the syringe assembly so as to displace the fluid from within the fluid region 14 of the syringe assembly.

Simultaneous with the displacement of the fluid from the fluid region 14, in the air region 15 side of the piston 31, pressure from the remaining air within the air region 15 is lowered due to the expanding volume without additional air influx due to the seals and the sealing of the one-way valve, creating a low pressure region 15 in the air region 15. Movement of the piston 31 toward the needle end of the syringe assembly may continue until substantially all of the fluid is discharged from the fluid region 14, at which time the connector 38 on the piston assembly 30 may contact the connector 29 on the needle assembly 20.

As the practitioner may moderately increase the applied axial force on the handle 60, in the direction of the needle assembly 20, two events may occur, substantially simultaneously or in no particular order. In the first event, the connector 38 on the piston assembly 30 may fully engage with the connector 29 on the needle assembly 20, thereby locking the piston assembly 30 with the needle assembly 20. In the second event, the needle assembly may move relative to the cylinder assembly 10, axially along the centerline 25, in the direction of the applied force for sufficient distance as to cause the retainer 16 to be sheared and the previously effected seal between the cylinder assembly 10 and the needle assembly 20 to be ruptured, thereby freeing the needle assembly 20 from engagement with the cylinder assembly 10. Continued axial pressure may be applied to the handle 60 so as to cause the needle assembly to "bottom-out" against the inner, piston side of the closure portion 13 of the cylinder assembly 10.

The movement of the piston 31 toward the needle assembly also has the effect of increasing the volume of the air region 15, which is sealed against entry of any external air into the volume of the air region 15, thereby creating a relatively low pressure region 15 within the cylinder body 11. The ruptured seal between the needle assembly 20 and the cylinder assembly 10 exposes the fluid region 14 in the cylinder assembly 10 to ambient atmospheric pressure. This atmospheric pressure acts upon the cross-sectional area of the piston 31 and seals 32, on the needle side of the piston 31. This force may be defined as a gross retracting force. In that the needle assembly 20 is disengaged from the cylinder assembly 10 and the needle assembly 20 is connected to the piston assembly 30, movement of the piston assembly 30 also results in corresponding movement of the needle assembly 20.

On the seal cap assembly 40 side of the piston assembly 30, two forces may work to oppose the gross retracting force. Regarding the first force, ambient atmospheric pressure may act upon the cross-sectional area of the piston stem 50, axially toward the needle assembly 20. Regarding the second force, the air pressure within the low pressure region 15 acts upon the cross-sectional area of the piston assembly 30, less the cross-sectional area of the piston stem 50. The combination of these two forces upon the piston assembly 30, in the direction of the needle assembly 20, act directionally in opposition to the gross retracting force, and the combined two forces in the direction of the needle assembly 20 may be referred to as an opposition force.

Because the pressure force acting on the piston assembly 30 in the low pressure region 15 is significantly less than the pressure on the piston assembly 30 in the fluid region 14, the difference in the gross retracting force and the opposition force may result in a net retracting force which acts upon the piston assembly 30 in the direction of the seal cap assembly 40.

Thus, as the practitioner relaxes the axial force applied to the handle 60, the net retracting force upon the piston assembly 30, acting in the direction of the seal cap assembly 40, may result in displacement of the piston assembly 30 and the connected needle assembly 20 in a direction toward the seal cap assembly 40. As the piston assembly 30 continues to move toward the seal cap assembly 40, the needle assembly 20 may be automatically, fully retracted into the cylinder assembly 10, as illustrated in FIG. 2A. In the event that a portion of the needle assembly 20 or the hypodermic needle 21 remains exposed beyond the end of the cylinder assembly 10 following completion of the automatic retraction, the practitioner may manually complete the retraction of the needle assembly 20 into the cylinder assembly 10 by exerting a small pull force upon the handle 60, along the center line 25, away from the needle assembly. After full retraction of the needle assembly 20 into the cylinder assembly 10, the unsupported needle assembly may gravitationally or otherwise, such as by spring lever (not shown), re-orient the tip of the needle 21 away from the center line 25, toward the inner wall 12 of the cylinder assembly 10. This reorientation may discourage or prevent the needle 21 from re-projecting from within the cylinder assembly 10.

When the needle assembly 20 is fully retracted into the cylinder assembly 10, the practitioner may also break the piston stem at a designated break point 53, substantially near the piston end of the stem 50. This may prevent the accidental manual projection of the needle assembly 20 from within the cylinder assembly 10. In addition, it may discourage subsequent use of a disposed syringe assembly for subsequent illegal drug use.

Figure 5:
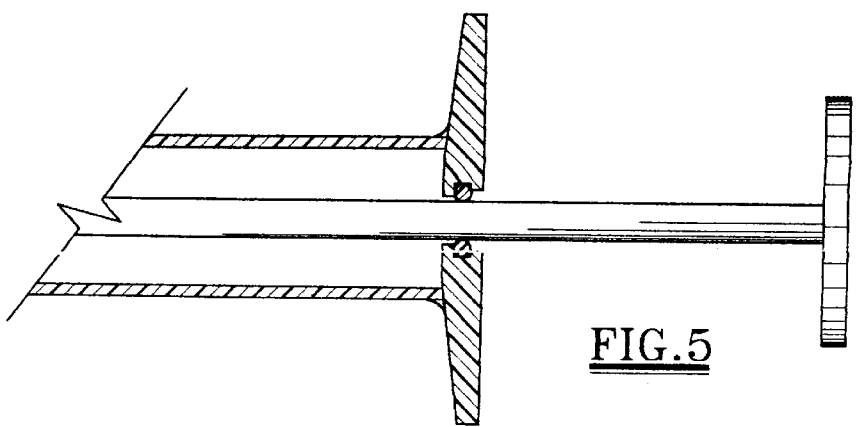
FIG. 5 is a cross-section view illustrating an alternative embodiment wherein the one-way valve assembly is incorporated into the port and stem seal.

Alternative embodiments of the seal cap assembly 40 may include a stem seal 42 which is formed as an integral part of the seal cap 47, or as illustrated in FIG. 5 and referring to FIG. 2, the stem seal 42 may also function as the one-way valve, which in turn may obviate the need for an additional valve port 45. Numerous other arrangements for the stem seal 42 are possible and are intended to be incorporated in this disclosure without an exhaustive listing of the same.

Figure 4:
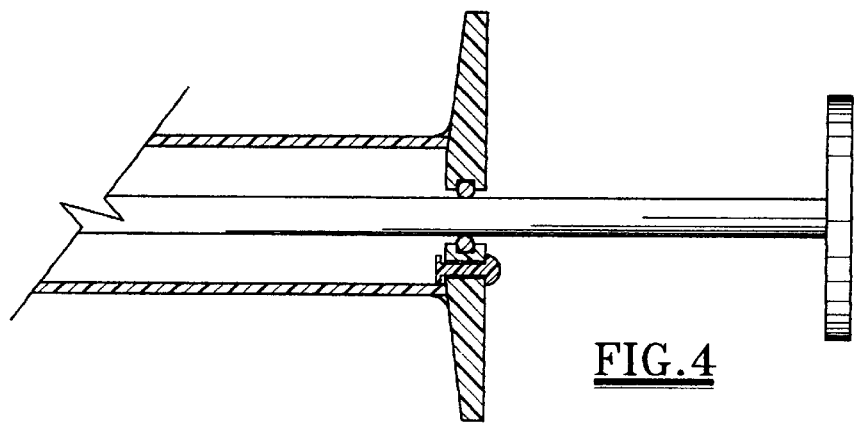
FIG. 4 is a cross-section view illustrating a duck-bill type valve arrangement.

A non-exhaustive list of alternative embodiments for the one-way valve 46 may include an umbrella type valve arrangement, as illustrated in FIG. 4; a reed type valve arrangement; a dart type valve; a flapper type valve arrangement, a ball, seat and cage type valve arrangement, a duck-bill valve arrangement as illustrated in FIGS. 2, 2A and 6; a poppet type valve arrangement, or any other type of check-valve arrangement. In addition, the valve port 45 may alternatively be located in the cylinder body 11, near the seal cap end of the cylinder assembly 10.

In an alternative embodiment of the syringe assembly as illustrated in FIG. 6 the seal cap assembly 40 may include a piston stop lever 64 to statically maintain the piston assembly in any desired axial position along the central axis 25. The piston stop lever 64 may include a port 65 to permit the piston stem 50 to penetrate the stop lever port 65. The piston stop lever 64 may be attached on one end, to the seal cap assembly 40 and may include a hinge between the stop lever 64 and the seal cap assembly 40, near the point of attachment, so as to allow the piston stop lever 64 to pivot relative to the seal cap assembly 40, axially along the center line 25. As the stop lever pivots, the edge of the stop lever port 65 may engage the outer surface 52 of the piston stem 50 so as to prevent axial movement of the piston stem 50. Referring to FIG. 6, when axial movement of the piston stem is desired, an axial force in the direction of the needle assembly 20 may be applied near the unattached end of the piston stop lever 64 causing the edge of the stop lever port 65 to disengage from the outer surface 52 of the piston stem 50, allowing the piston stem 50 to axially move through the stop lever port 65.

Alternative embodiments of the syringe assembly as illustrated in FIGS. 3, 4, 5, and 6 may include a varying arrangements with respect to all or any of the cylinder assembly 10, the needle assembly 20 and/or the piston assembly 30. In the embodiment illustrated in FIG. 3, the cylinder assembly 10 may include a cylinder body 11 having a needle end and a through bore along a central axis 25 of the syringe assembly. The cylinder assembly 10 may include a closure portion 75 which is not frustoconical tapered as illustrated in FIG. 2. The closure portion 75, as illustrated in FIG. 3, may include a substantially blunt or flange type closure, including a portal opening 77, substantially alone the central axis 25, the portal opening 77 for penetration by a needle assembly or portions of a needle assembly, such as a hypodermic needle 21. The closure portion 75 may include an axial extension 76 along the center line 25 to assist in supporting the needle 21.

In addition, an alternative embodiment, as illustrated in FIG. 3, may include a needle assembly 70 having a hypodermic needle 21 which may be engaged with a substantially cylindrical needle support 72. The needle support 72 may include a releasing ring 71 for shearing a shearable retainer 86, the shearable retainer 86 being positioned by and supported by a radial retainer supporting projection 87. The needle support 72, releasing ring 71, shearable retainer 86 and radial retainer supporting projection 87 each having a through bore, substantially along the central axis 25 of the syringe assembly. The needle support 72 may include a connector 73 which may generally be described as a male connector. The piston assembly 30 may alternatively include a connector 83 which may generally be described as a radial female connector for engagement with the male connector 73. In alternative embodiments, connectors on the needle assembly and the piston assembly may engage using any of various engagement components or mechanisms other than by generally male and female components. Male and female components are provided for illustrative purposed only and not exclusive as to connector embodiments.

It may be appreciated that various changes to the methods or steps herein, as well as in the details of the illustrated methods and systems may be made within the scope of the attached claims without departing from the spirit of the invention. While preferred embodiments of the present invention have been described and illustrated in detail, it is apparent that still further modifications and adaptations of the preferred embodiments will occur to those skilled in the art. However, it is to be expressly understood that such modifications and adaptations are within the spirit and scope of the present invention, which is set forth in the following claims.

What is claimed:

1. An improved syringe assembly, comprising:
   a cylinder body having a needle end and a seal cap end, the cylinder body having a central axis and an internal through bore extending between the needle end and the seal cap end;
   a retainer adjacent the needle end of the cylinder body;
   a needle assembly including a hypodermic needle and needle support, the needle support being in scaled engagement with the needle and releasably retaining the needle assembly in sealed engagement with the cylinder body by the retainer;
   a piston assembly having a needle end and a seal cap end and including a piston for coaxial telescopic movement of the piston assembly within the internal through bore, and one or more piston seals for effecting a pneumatic seal between the piston and an inner wall of the cylinder body;
   a connector for selectively attaching the piston assembly to the needle assembly;
   a piston stem having a piston end and a handle end with the piston end attached to the piston assembly for axially moving the piston assembly within the through bore of the cylinder body;
   a handle attached to the handle end of the piston stem;
   a seal cap assembly attached to the seal cap end of the cylinder body, the seal cap assembly including a seal cap having a piston side and a stem handle side, the seal cap being in pneumatic sealing engagement with the seal cap end of the cylinder body for effecting a pneumatically sealed chamber inside of the cylinder body between the piston assembly and the seal cap assembly, the seal cap assembly including a port for telescopic movement of the piston stem through the port, and including a seal for effecting a pneumatic seal between the seal cap and the piston stem; and
   a one-way valve for evacuation of air from within the internal through bore between the piston assembly and the seal cap assembly while prohibiting the entry of air into the internal through bore of the cylinder body.

2. The syringe assembly as defined in claim 1, wherein the cylinder body further comprises:
   a frustoconical closure portion having a through bore on the needle end of the cylinder body for supporting and stabilizing the needle assembly within the cylinder body.

3. The syringe assembly as defined in claim 1, wherein the connector includes a male connector and a female connector.

4. The syringe assembly as defined in claim 3, wherein the male connector is secured to the piston and the female connector is secured to the needle assembly.

5. The syringe assembly as defined in claim 1, wherein the one-way valve forms a seal between the seal cap and the piston stem.

6. The syringe assembly as defined in claim 1, wherein the one-way valve is positioned within the seal cap assembly.

7. The syringe assembly as defined in claim 1, wherein the piston stem includes a weakened portion for breaking off the piston stem near the piston end.

8. The syringe assembly as defined in claim 1, further comprising:
a stop-lever substantially adjacent the seal cap, wherein the stop level selectively engages the piston stem for temporarily fixing the axial position of the piston relative to the cylinder body.

9. An improved syringe assembly, comprising:
a cylinder body having a needle end and a seal cap end, the cylinder body having a central axis and an internal through bore extending between the needle end and the seal cap end;
a needle assembly including a hypodermic needle and needle support, the needle support being in sealed engagement with the needle and releasably retained within the needle end of the cylinder body;
a piston assembly having a needle end and a seal cap end and including a piston for coaxial telescopic movement of the piston assembly within the internal through bore, and one or more piston seals for effecting a pneumatic seal between the piston and an inner wall of the cylinder body;
a piston connector mechanically attached to the piston assembly;
a needle connector mechanically attached to the needle assembly and selectively attachable to the piston connector;
a piston stem having a piston end and a handle end with the piston end attached to the piston assembly for axially moving the piston assembly within the through bore of the cylinder body along the central axis;
a seal cap assembly including a seal cap having a piston side and a stem handle side, the seal cap being in pneumatic sealing engagement with the seal cap end of the cylinder body for effecting a pneumatically sealed chamber inside of the cylinder body between the piston assembly and the seal cap assembly, the seal cap assembly including a port for telescopic movement of the piston stem through the port, and the seal cap assembly including a seal for effecting a pneumatic seal between the port and the piston stem; and
a one-way valve for evacuation of air from within the internal through bore between the piston assembly and the seal cap assembly and to prohibit the entry of air into the internal through bore of the cylinder body.

10. The syringe assembly as defined in claim 9, wherein the cylinder body further comprises:
a frustoconical closure portion having a through bore on the needle end of the cylinder body for supporting and stabilizing the needle assembly within the cylinder body.

11. The syringe assembly as defined in claim 9, wherein the connector includes a male connector and a female connector.

12. A method of operating a hypodermic needle inside of a cylinder body having a through bore, a needle end and a seal cap end, the method comprising:
positioning a needle assembly including a hypodermic needle, a needle support and a needle connector within the needle end of the cylinder body;
positioning a piston assembly within the cylinder body, the piston assembly including a piston, one or more piston seals, a piston stem and a piston connector;
inserting the hypodermic needle into a source of fluid;
moving the piston assembly from the needle end of the cylinder body toward the seal cap end of the cylinder body, thereby drawing fluid through the needle assembly into a fluid region inside of the cylinder body and simultaneously displacing air from an air region in the cylinder body through a one-way valve assembly;
inserting the hypodermic needle with the drawn fluid within the cylinder body into a fluid repository;
applying a force upon the piston stem to move the piston assembly toward the needle end of the cylinder body, thereby displacing fluid from within the fluid region in the cylinder body and simultaneously expanding the volume of the air region in the cylinder body without permitting the entry of substantially any air into the air region of the cylinder body, thereby lowering the air pressure in the air region of the cylinder body;
connecting the needle connector to the piston connector;
releasing the needle assembly from its position in the cylinder body; and
reducing the applied axial force upon the piston stem to allow the piston assembly and connected needle assembly to move from the needle end of the cylinder body toward the seal cap end of the cylinder body, thereby retracting the needle assembly into the cylinder body.

13. The method defined in claim 12, wherein releasing the needle assembly from the cylinder body includes shearing a retainer which connected the needle assembly to the cylinder body.

14. The method defined in claim 12, wherein releasing the needle assembly from the cylinder assembly includes breaking a friction fit between the needle assembly and the cylinder body.

15. The method defined in claim 12, wherein retracting the needle assembly further comprises applying a force to the piston stem to fully retract the needle assembly into the cylinder body.

16. The method as defined in claim 12, further comprising:
breaking the piston stem after use of the syringe.

* * * * *